United States Patent [19]

Fischer et al.

[11] Patent Number: 4,585,876
[45] Date of Patent: Apr. 29, 1986

[54] NOVEL XANTHONES AND THIOXANTHONES

[75] Inventors: Walter Fischer, Reinach, Switzerland; Jürgen Finter, Freiburg, Fed. Rep. of Germany; Hans Zweifel, Basel, Switzerland

[73] Assignee: Ciba-Geigy Corporation, Ardsley, N.Y.

[21] Appl. No.: 551,768

[22] Filed: Nov. 14, 1983

[30] Foreign Application Priority Data

Nov. 25, 1982 [CH] Switzerland .......................... 6872/82

[51] Int. Cl.$^4$ .................. C07D 311/86; C07D 335/16; C07D 495/04; C07D 491/04
[52] U.S. Cl. ..................................... 548/423; 549/25; 548/478; 548/480; 549/27; 549/235; 549/392; 549/393; 522/50; 522/52; 522/53; 522/904; 522/63; 522/55; 522/57; 522/59; 522/14; 522/16; 522/81; 522/101; 522/152; 522/167; 522/168; 562/432; 562/435; 562/473; 562/474; 260/465 D; 260/465 E; 260/465 F; 260/465 H; 548/471; 548/473; 548/475; 548/477
[58] Field of Search .................. 548/423, 426; 549/23, 549/25, 224, 225, 383, 235, 392, 393

[56] References Cited

U.S. PATENT DOCUMENTS

| | | | |
|---|---|---|---|
| 2,701,801 | 2/1955 | Boyd | 548/426 |
| 3,524,863 | 8/1970 | Huffman et al. | 548/423 |
| 3,534,063 | 10/1970 | Hoffman et al. | 549/392 |
| 3,544,303 | 12/1970 | Swidler et al. | 548/423 |
| 3,818,042 | 6/1974 | Pfister et al. | 549/393 |
| 3,922,284 | 11/1975 | Heath et al. | 548/476 |
| 4,011,246 | 3/1977 | Markezich | 549/243 |
| 4,250,182 | 2/1981 | Gorvin | 114/379 |
| 4,254,144 | 3/1981 | Markley | 514/524 |
| 4,257,953 | 3/1981 | Wolliams, III et al. | 568/723 |
| 4,363,917 | 12/1982 | Fischer et al. | 548/480 |

FOREIGN PATENT DOCUMENTS

| | | | |
|---|---|---|---|
| 110832 | 6/1984 | European Pat. Off. | 548/423 |
| 138754 | 4/1985 | European Pat. Off. | 549/27 |
| 216480 | 4/1908 | Fed. Rep. of Germany | 549/25 |
| 634841 | 2/1983 | Switzerland | 549/25 |
| 956014 | 4/1964 | United Kingdom | 549/25 |

Primary Examiner—Mark L. Berch
Assistant Examiner—G. Hendricks
Attorney, Agent, or Firm—Michael W. Glynn; Irving M. Fishman

[57] ABSTRACT

Novel xanthones and thioxanthones of the formula I

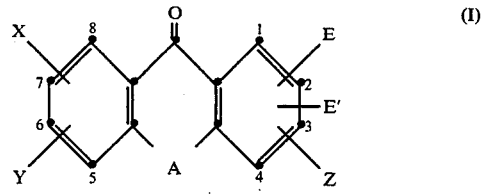

in which A, X, Y, Z, E and E' are as defined in patent claim 1, are described. A is preferably —S— and E and E' are preferably bonded in the ortho-position relative to one another. The compounds (I) are suitable, for example, as sensitizers for photocrosslinkable polymers or photocurable compositions, or for use in mixtures with polymers with H donor groups for image formation, in particular electrically conductive coatings and patterns, by means of electroless deposition of metals.

7 Claims, No Drawings

NOVEL XANTHONES AND THIOXANTHONES

The present invention relates to novel xanthones and thioxanthones, a process for their preparation, the novel intermediates which can thereby be obtained and the use of the novel xanthones and thioxanthones.

The present invention relates to xanthones and thioxanthones of the formula I

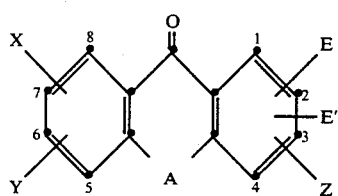

in which A is —O— or —S—, X and Y independently of one another are hydrogen, $C_{1-20}$-alkyl, halogen, —OR', —SR' or —NO$_2$, Z is hydrogen, $C_{1-4}$-alkyl, halogen, —OR', —SR', —NO$_2$, —NH$_2$, —OH or —NHCOCH$_3$, E and E' independently of one another are —COOR'', —CON(R'')$_2$ or —CN or together are —CO—O—CO— or —CO—N(R)—CO—, R is hydrogen, $C_{1-20}$-alkyl, phenyl, alkylphenyl having 1–4 C atoms in the alkyl moiety, phenethyl, benzyl, cyclohexyl, —(CH$_2$)$_n$—Q, $C_{2-6}$-alkenyl, propargyl, —N(CH$_3$)$_2$, —OH or $C_{1-10}$-alkoxy, R' is $C_{1-20}$-alkyl, phenyl, halogenophenyl, nitrophenyl, alkyl- or alkoxyphenyl having in each case 1–4 C atoms in the alkyl or alkoxy moiety, benzyl or phenethyl, the radicals R'' independently of one another are hydrogen, M$^+$, $C_{1-20}$-alkyl, alkoxyalkoxy alkyl having 3–10 C atoms or hydroxyalkyl having 2–8 C atoms, n is the number 1, 2 or 3, Q is —OH, —N($C_{1-3}$-alkyl)$_2$, —SO$_3$—M$^+$, —OCOCH=CH$_2$ or —OCOC(CH$_3$)=CH$_2$ and M$^+$ is an alkali metal cation, and, if A is —O—, E and E' together are —CO—O—CO— or —CO—N(R)—CO—.

Alkyl groups X, Y, R, R' and R'' having 1–20 C atoms can be straight-chain or branched groups, for example methyl, ethyl, n-propyl, isopropyl, n-butyl, sec.-butyl, tert.-butyl, n-pentyl, 2- or 3-pentyl, n-hexyl, 2-ethylhexyl, n-heptyl, 2- or 3-heptyl, n-octyl, 1,1,3,3-tetramethylbutyl, n-nonyl, n-decyl, 2-decyl, n-dodecyl, n-tetradecyl, n-hexadecyl, n-octadecyl, tridec-7-yl, heptadec-9-yl, 2,6,10-trimethyldodecyl and 2,6,10,14-tetramethylhexadecyl. Alkyl groups X, Y, R, R' and R'' preferably have 1–10 C atoms. Alkoxy groups R can likewise be straight-chain or branched, such as the methoxy, ethoxy, n-propoxy, isopropoxy, n-butyloxy, sec.-butyloxy, n-pentyloxy, n-hexyloxy, 2-ethylhexyloxy, n-octyloxy and n-decyloxy group. Straight-chain alkoxy groups R having 1–4 C atoms are preferred.

Halogen atoms X, Y or Z or as substituents on these radicals are, for example, fluorine and, in particular, bromine or chlorine atoms.

A $C_{1-4}$-alkyl radical Z is, for example, methyl, ethyl, n-propyl, isopropyl or n-butyl, in particular ethyl and especially methyl.

Alkylphenyl groups R and R' and alkoxyphenyl groups R are, in particular, such groups with 1 or 2 C atoms in the alkyl or alkoxy moiety, such as methylphenyl, ethylphenyl and methoxy- and ethoxy-phenyl.

A phenethyl radical R is, in particular, the 2-phenethyl group. A $C_{2-6}$-alkenyl radical R is, for example, the vinyl, allyl, methallyl, buten-1-yl or hexen-1-yl group.

An alkoxyalkoxyalkyl or hydroxyalkyl group R'' is for example, methoxymethoxymethyl, methoxy-2-methoxyethyl, 2-(2-methoxyethoxy)-ethyl, 2-(2-ethoxyethoxy)-ethyl, 2-(3-propoxyethoxy)-ethyl or 2-(4-butoxyethoxy)-ethyl; 2-hydroxyethyl, 2- or 3-hydroxypropyl, 4-hydroxybutyl, 3-hydroxybutyl, 5-hydroxypentyl, 2-hydroxyhexyl or 8-hydroxyoctyl. Alkoxyalkoxyalkyl groups R'' preferably have 5–10 C atoms; the 2-(2-methoxyethoxy)-ethyl and 2-(2-ethoxyethoxy)-ethyl groups are particularly preferred.

An alkali metal cation M is, in particular, the potassium or sodium cation.

A is preferably —S—; X and Y preferably independently of one another are hydrogen, chlorine, bromine, $C_{1-4}$-alkyl or —NO$_2$. X and Y are particularly preferably each hydrogen.

Preferred meanings of Z are hydrogen, $C_{1-4}$-alkyl, chlorine, bromine, $C_{1-10}$-alkoxy, $C_{1-10}$-alkylthio, phenylthio, —NO$_2$, —NH$_2$ or —OH.

R is preferably hydrogen, $C_{1-10}$-alkyl, phenyl, tolyl, benzyl, —(CH$_2$)$_n$—Q where n=2 or 3 and Q=—OH, —SO$_3$—Na$^+$, —N(CH$_3$)$_2$, —N(C$_2$H$_5$)$_2$; —OCOCH=CH$_2$ or OCOC(CH$_3$)=CH$_2$; or $C_{2-6}$-alkenyl, in particular allyl, propargyl, or —N(CH$_3$)$_2$.

Preferred compounds of the formula I are those in which X and Y are hydrogen, A is —S— and halogen atoms Z or halogen substituents in Z are fluorine, chlorine or bromine, in particular chlorine or bromine.

E and E' are preferably bonded in adjacent positions to one another or in the 1,3-position. Preferred compounds are those in which X and Y are hydrogen, A is —S—, Z is hydrogen, chlorine, —NO$_2$, —NH$_2$, —OH, —OR' or —SR', E and E' are bonded in adjacent positions to one another and independently of one another are a —COOR'' group or together are —CO—O—CO— or —CO—N(R)—CO, R is as defined under formula I, R' is $C_{1-10}$-alkyl, benzyl, phenyl or tolyl, and the radicals R'' independently of one another are hydrogen, M$^+$, $C_{1-10}$-alkyl or alkoxyalkoxyalkyl having 5–10 C. atoms.

Particularly preferred compounds are those of the formula Ia

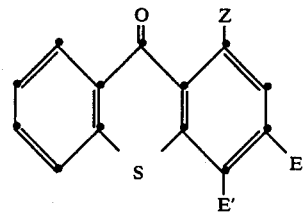

in which Z is hydrogen, chlorine, —NO$_2$, —NH$_2$, —OH or —SR', R' is $C_{1-10}$-alkyl or phenyl, E and E' independently of one another are —COOR'' or together are —CO—O—CO— or —CO—N(R)—CO—, the radicals R'' independently of one another are hydrogen, M$^+$, $C_{1-10}$-alkyl or alkoxyalkoxyalkyl having 5–10 C atoms and R is as defined under formula I, especially compounds of the formula Ia in which Z is hydrogen, E and E' independently of one another are —COOR'' or together are —CO—O—CO— or —CO—N(R)—CO—, R is hydrogen, $C_{1-10}$-alkyl, phenyl, tolyl, benzyl, —(CH$_2$)$_n$—OH, —(CH$_2$)$_n$—N($C_{1-2}$-alkyl)$_2$ where n=2 or 3, —CH$_2$CH$_2$OCOC(CH$_3$)=CH$_2$, allyl or propargyl and the radicals R″ independently of one another are hydrogen, Na+, $C_{1-10}$-alkyl or $C_{1-2}$-alkoxy-$C_{1-3}$-alkoxy-$C_{1-2}$-alkyl. The compound of the formula Ia in which Z is hydrogen and E and E′ together are —CO—N(CH₂CH=CH₂)—CO— is very particularly preferred.

The compounds of the formula I can be prepared, for example, by (a) if E and E′ are bonded in adjacent positions to one another, reacting a compound of the formula II

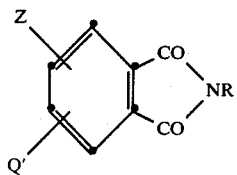
(II)

with a compound of the formula III

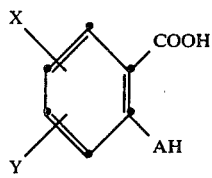
(III)

or with a salt thereof, in the presence of a base to give a compound of the formula IV

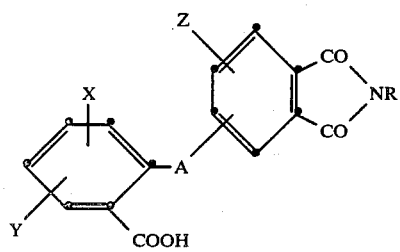
(IV)

cyclising the compound of the formula IV, if necessary after first converting it into the acid chloride, to give a compound of the formula Ib

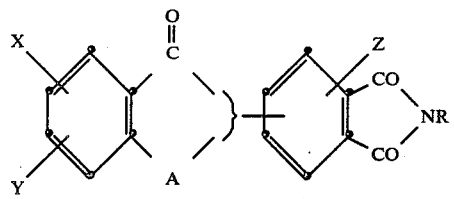
(Ib)

and, if appropriate, then converting this into a compound of the formula I in which E and E′ independently of one another are —COOR″, —CON(R″)₂ or —CN or together are —CO—O—CO— or —CO—N(-R)—CO—, where R has different meanings, or (b) to prepare compounds of the formula I in which E and E′ independently of one another are —COOR″, —CON(R″)₂ or —CN, reacting a compound of the formula IIa

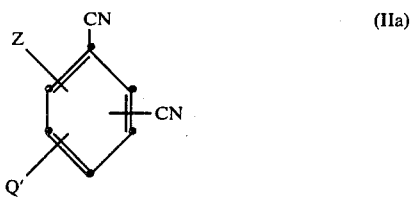
(IIa)

with a compound of the formula III or with a salt of a compound of the formula III, in the presence of a base to give a compound of the formula IVa

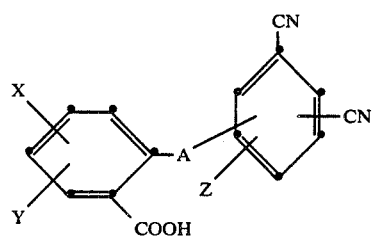
(IVa)

cyclising the compound of the formula Iva to give a compound of the formula Ic

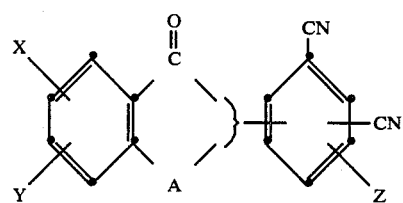
(Ic)

and, if appropriate, then converting this into a compound of the formula I in which E and E′ independently of one another are —COOR″ or —CON(R″)₂, (c) reacting a compound of the formula IIb

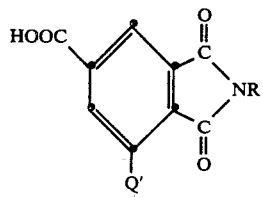
(IIb)

with a compound of the formula IIIa

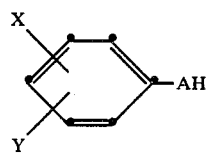
(IIIa)

or with a salt thereof, in the presence of a base, to give a compound of the formula IVb

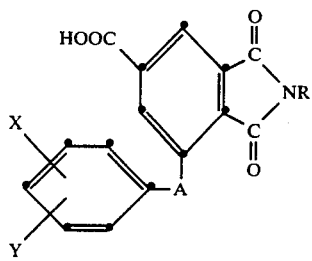

converting the compound of the formula IVb into the dicarboxylic acid by hydrolysis and converting this dicarboxylic acid into the anhydride, which is cyclised to a compound of the formula Ic

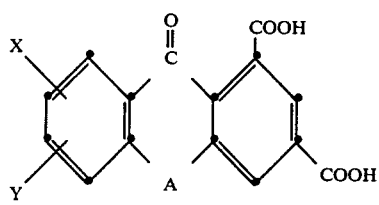

and, if appropriate, then converting this compound of the formula Ic to a compound of the formula I in which E and E' are —COOR" or —CON(R")$_2$, A, X, Y, Z and R being as defined under formula I and Q' being —NO$_2$ or a halogen atom.

Compounds of the formula II or IIb where Q'=—NO$_2$ are preferably used for the preparation of compounds of the formula I in which E and E' are bonded in the 1,3- or 3,4-position. Compounds of the formula II where Q'=chlorine are preferably used for the preparation of compounds of the formula I in which E and E' are bonded in the 1,2- or 2,3-position.

The reaction of the compounds of the formula II, IIa or IIb with the compounds of the formula III or IIIa or salts thereof is advantageously carried out in the presence of an inert organic solvent, for example N,N-dialkylamides of aliphatic monocarboxylic acids having 1-3 C atoms in the acid moiety, for example, N,N-dimethylformamide and N,N-dimethylacetamide; dialkylsulfoxides, for example dimethylsulfoxide and diethylsulfoxide; aliphatic or cyclic ethers, for example diethyl ether, di-isopropyl ether, dimethoxyethane, tetrahydrofuran and dioxane; and cyclic amides, such as N-methylpyrrolidone or N-ethylpyrrolidone. Preferred solvents are N,N-dimethylformamide and tetrahydrofuran.

Salts of compounds of the formula III are both salts with organic bases and salts with inorganic bases. Alkali metal salts and quaternary ammonium salts, such as the Na, K and tetramethyl-, tetraethyl-, benzyltrimethyl- and benzyltriethyl-ammonium salts, are preferred. The above salts can be used as such or can be formed in situ in a manner which is known per se. The compound of the formula III are preferably used in the form of their disodium salts. If the compounds of the formula III are used as the free acids, the reaction is carried out in the presence of an inorganic or organic base, such as triethylamine, sodium fluoride or carbonate or potassium fluoride or carbonate.

The cyclisation of the compounds of the formulae IV, Iva and Ivb is preferably carried out in the presence of a proton acid or a Lewis acid. Examples of suitable proton acids are polyphosphoric acid, by itself or as a mixture with phosphorus oxychloride, and chlorosulfonic acid and sulfuric acid. Examples of suitable Lewis acids are aluminium trichloride and boron trifluoride. Cyclisation in the presence of polyphosphoric acid or aluminium trichloride is preferred. Cyclisation in the presence of a Lewis acid, such as aluminium trichloride, is advantageously carried out in the presence of an inert organic solvent. Particularly suitable solvents are chlorinated aliphatic or aromatic hydrocarbons, such as methylene chloride, 1,2-dichloroethane, 1,2,3-trichloropropane, 1,1,2,2-tetrachloroethane, chlorobenzene and the dichlorobenzenes; and nitromethane, nitrobenzene and carbon disulfide. If a proton acid is used as the cyclising agent, the reaction is advantageously carried out in an excess of the acid, in particular an excess of polyphosphoric acid.

The conversion of compounds of the formula Ib into compounds of the formula I where R has a different meaning, or into compounds of the formula I or Id in which E and E' independently of one another are —COOR", —CON(R")$_2$ or —CN or together are —CO—O—CO— can be carried out in a manner which is known per se, for example as follows: E/E'-=—COOH or together —CO—O—CO—: by hydrolysis in the presence of suitable bases, such as KOH or NaOH, and subsequent cyclisation in the presence of conventional dehydrating agents, such as acetic anhydride, or by heating, in the presence or absence of a suitable solvent, such as the xylenes; E/E'-=—CON(R")$_2$: by reaction with suitable primary or secondary amines; E/E'=—COOR", where R"=hydrogen: by reaction with suitable alcohols; compounds of the formula I where R has a different meaning: by reaction of the anhydrides with amines NH$_2$—R or by reaction of compounds of the formula I/Ib in which R is hydrogen with corresponding halides; E/E'=—CN: by reaction of the corresponding carboxylic acids with ammonia in the presence of dehydrating catalysts or by treatment of the corresponding acid amides with agents which detach water, such as P$_2$O$_5$; Q.=—O-COCH=CH$_2$ or —OCOC(CH$_3$)=CH$_2$; by reaction of the corresponding ω-hydroxyalkylimides with acrylyl chloride or methacrylyl chloride.

If desired, compounds of the formula Ic can be hydrolysed to the carboxylic acid amides or carboxylic acids in a manner which is known per se.

Groups X, Y and Z in compounds of the formula I, Ib, Ic, Id or IV can also be converted into different groups X, Y or Z by methods which are known per se. Thus, for example, nitro groups X, Y or Z can be converted into —SR' groups by reaction with mercaptans or salts thereof, or nitro groups Z can be reduced to amino groups, or converted into OH groups by reaction with alkali metal carbonates or acetates. Chlorinating agents which are known per se, such as thionyl chloride, phosgene, or, preferably, oxalyl chloride, can be used for any conversion of the compounds of the formula IV into acid chlorides.

The compounds of the formulae IV and IVa are novel, and are likewise the subject of the present invention. The above statements apply in respect of preferred meanings of A, X, Y, Z and R. The starting substances of the formulae II, IIa and III are known, or they can be prepared by methods which are known per se. The invention also relates to the novel compounds of the formula Ivc:

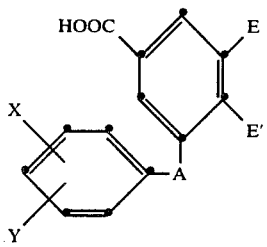

if X and Y are as defined above and E and E' together are —CO—O—CO— or CO—NR—CO—.

The compounds of the formula I are used, for example, as photosensitisers for various types of photocrosslinkable polymers. They have a high photosensitivity and are particularly compatible with the polymers. As a result of the unexpected bathochromic shift of their absorption, the thioxanthone-anhydrides and -imides of the formula I are particularly suitable for applications in which long-wavelength UV light (up to about 450 nm) is used for irradiation.

Polymers which can be crosslinked under the action of light are used, for example, for the production of printing plates for offset printing and for the preparation of offset photo-lacquers, for unconventional photography, for example by producing photographic images by means of photopolymerisation or photocrosslinking. Such polymers are used, in particular, as so-called photoresists for the production of printed circuits by methods which are known per se. The side of the printed circuit board provided with the photosensitive layer is exposed to light through a negative slide bearing the conductor pattern and is then developed, after which the non-exposed areas of the layer are removed by developer liquid. Such applications, including the particularly suitable, photosensitive polymers, are described, for example, in German Offenlegungsschrift No. 3,117,568 (A1).

The compounds of the formula I, in particular the thioxanthone-anhydrides and -imides, can also be used as sensitisers for photocurable compositions, which may or may not be coloured. Such compositions preferably contain a photopolymerisable binder, in particular an olefinically unsaturated binder, where relevant a pigment or dye, and a photoinitiator, for example a photoinitiator of the formula V

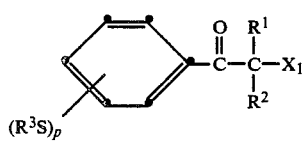

in which p is the number 2 or, in particular, 1, $R^3$ is hydrogen, $C_1$-$C_{12}$-alkyl, $C_3$-$C_6$-alkenyl, $C_5$-$C_6$-cycloalkyl, $C_7$-$C_9$-phenylallyl, phenyl or phenyl which is substituted by —COO($C_1$-$C_4$-alkyl), or a —CH$_2$C-H$_2$OH, —CH$_2$CH$_2$—OOC—CH=CH$_2$, —CH$_2$CN, —CH$_2$COOH, —CH$_2$COO($C_1$-$C_8$-alkyl), —CH$_2$CH$_2$CN, —CH$_2$CH$_2$COO($C_1$-$C_8$-alkyl),

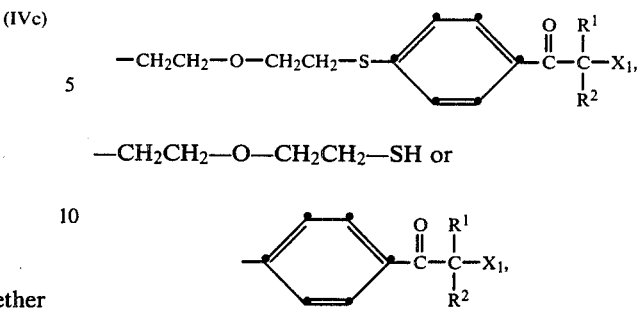

—CH$_2$CH$_2$—O—CH$_2$CH$_2$—SH or $R^1$ and $R^2$ independently of one another are $C_1$-$C_4$-alkyl, phenyl or $C_7$-$C_9$-phenylalkyl, $R^1$ and $R^2$ together are $C_2$-$C_8$ alkylene, and $X_1$ is an amino group —N($R^4$)($R^5$), in which $R^4$ is $C_1$-$C_8$-alkyl, $C_2$-$C_4$-alkyl which is substituted by OH, $C_1$-$C_4$-alkoxy or CN, or $C_3$-$C_5$-alkenyl and $R^5$ has one of the meanings of $R^4$ or, together with $R^4$, is $C_4$-$C_5$-alkylene, which can be interrupted by —O—, —S— or —N($R^6$)— in which $R^6$ is $C_1$-$C_4$-alkyl, 2-cyanoethyl, 2-hydroxyethyl or 2-hydroxypropyl.

Preferred compounds of the formula V are those in which p is the number 1, $R^3$S— is methylthio or 2-hydroxyethylthio bonded in the 4-position, $R^1$ and $R^2$ are each methyl or ethyl and $X_1$ is the morpholino group. The compounds of the formula V can be prepared by methods similar to those known from European Patent Application Publication No. 3,002, by introducing the amino group $X_1$ into corresponding sulfur-containing phenyl alkyl ketones. The amount of photoinitiator in the photocurable compositions is advantageously 0.1–20% by weight, preferably 1–6% by weight.

Examples of suitable photopolymerisable binders (photopolymerisable compounds) are described in German Offenlegungsschrift 3,117,568 (A1) which has already been mentioned. The pigments which are also used where relevant can be inorganic or organic, such as titanium dioxide, carbon black or metal powders, monoazo or disazo pigments, phthalocyanine pigments or pigments of the perylene, thioindigo, quinacridone or triphenylmethane series. Examples of dyes are azo dyes, azomethine dyes, anthraquinone dyes and metal complex dyes.

Photocurable compositions of the type described above, which may or may not be coloured, can be used for various purposes, in particular for printing inks, especially for offset printing, screen printing or gravure printing, and also as coating agents or photoresists.

A further important field of use of the compounds of the formula I is their use as photo-redox catalysts in various oxidation/reduction reactions or in photosensitive coating materials. However, together with polymers with H donor groups, they are particularly suitable for image formation by the action of light on various organic or inorganic substrates, in particular for producing electrically conductive coatings or patterns, especially printed circuits, by means of electroless deposition of metals.

Examples of suitable substrates for image formation are glass, metals and metal oxides, such as aluminium, aluminium oxide and copper, ceramics, paper and high molecular weight organic materials. High molecular weight organic materials are natural and synthetic polymers, for example cellulose materials, such as cellulose acetates, cellulose propionates, cellulose butyrates and cellulose ethers, such as methyl cellulose; polymers derived from α,β-unsaturated acids, such as polyacrylates and polymethacrylates, polyacrylamides and polyacrylonitrile; styrene polymers and copolymers thereof, for example styrene/butadiene copolymers and acrylonitrile/butadiene/styrene copolymers; vinyl and vinylidene polymers and copolymers thereof, such as polyvinyl chloride, polyvinylidene chloride, vinyl chloride/vinylidene chloride copolymers and vinyl chloride/vinyl acetate copolymers; polymers derived from unsaturated alcohols and amines and derivatives thereof, such as polyvinyl alcohol, polyvinyl acetate and polyallylmelamine; crosslinked epoxide resins; polyacetals; polyalkylene oxides and polyphenylene oxides; polyamides, polyimides, polyamide-polyimide block copolymers, polysulfones and polyesters; alkyd resins, for example glycerol/phthalic acid resins and mixtures thereof with melamine/formaldehyde resins; and melamine/formaldehyde, urea/formaldehyde and phenol/formaldehyde resins and the like.

Polymers with H donor groups are polymerisation, polycondensation or polyaddition products with free OH, NH or alkylamino groups, in particular —N(CH$_3$)$_2$ groups, such as polymerisation products of hydroxyalkyl (meth)acrylates or (meth)acrylic acid hydroxyalkylamides with other olefinically unsaturated monomers, such as (meth)acrylic acid, (meth)acrylic acid esters and (meth)acrylonitrile; and furthermore partially hydrolysed cellulose acetates or gelatin, and adducts of diphenols, dicarboxylic acids or diamines with diglycidyl ethers, in particular diglycidyl ethers of bisphenol A, which may or may not be prelengthened.

To produce electrically conductive coatings or patterns by means of electroless deposition of metals, mixtures of compounds of the formula I and polymers with H donor groups and, if appropriate, metal salts of groups Ib and VIII of the Periodic Table, in particular copper salts, are exposed to light. The amount of compound of the formula I is advantageously 0.1 to 20% by weight, based on the mixture of polymer and compound of the formula I. Under the action of light, the compounds of the formula I are reduced to free radicals, which can in turn reduce other compounds, such as the above metal salts. Electrically conductive metallic coatings or patterns can then be produced in the conventional manner, by electroless deposition of metals, such as copper, nickel, cobalt, silver, tin and the like, on the free radicals or zero-valent non-conductive metal nuclei (non-conductive visible image points) thereby obtained. If desired, these metallic coatings or patterns can be thickened by electrolytic deposition of metals using conventional metal deposition baths. It was not hitherto known that xanthones and thioxanthones can reduce photochemically the metal ions of the type mentioned. Compounds of the formula I with suitable functional groups, for example anhydride or —(CH$_2$)$_n$—OCOCH=CH$_2$ and —(CH$_2$)$_n$—OCOC(CH$_3$)=CH$_2$ groups, can also be incorporated chemically into polymers or polymerised with other ethylenically unsaturated monomers. If polymers of this type have H donor groups, advantageously in about 20% of the recurring structural elements, they can likewise be used as described above for image formation by means of electroless deposition of metals (with or without the addition of metal salts of groups Ib and VIII of the Periodic Table).

Any suitable light sources, for example xenon lamps, metal halide lamps and, in particular, high-pressure and medium-pressure mercury lamps, can be used for the exposure to light in the applications mentioned above.

EXAMPLE 1

(a) 40.0 g of 3-nitrophthalimide and 49.5 g of disodium thiosalicylate (prepared by dissolving thiosalicylic acid in 2 equivalents of 1N sodium hydroxide solution and evaporating, finally twice with xylene) are stirred in 200 ml of N,N-dimethylformamide (DMF) at 80° C. for 8 hours. The mixture is evaporated at 70° C. in a rotary evaporator and the residue is triturated with 2N hydrochloric acid, while stirring. The precipitate is filtered off, washed with water and dried. After recrystallisation from dioxane, 50.2 g (81% of theory) of 3-(2-carboxyphenylthio)-phthalimide are obtained; melting point: 289°-290° C.

Analysis for $C_{15}H_9NO_4S$ (molecular weight: 299.30): calculated: C 60.19, H 3.03, N 4.67, O 21.38, S 10.71%, found: C 59.55, H 3.16, N 4.57, O 21.49, S 10.46%.

(b) 20.0 g (66.8 mmol) of 3-(2-carboxyphenylthio)-phthalimide are suspended in 130 g of polyphosphoric acid and the suspension is stirred at 150° C. for 90 minutes. The reaction mixture is cooled and stirred carefully with 500 ml of water and the precipitate is filtered off and washed several times with water. After drying in a vacuum drying cabinet at 150° C., the product is recrystallized from xylene. 12.4 g (66% of theory) of thioxanthone-3,4-dicarboxylic acid imide are obtained; melting point: 348°-350° C.

Analysis for $C_{15}H_7NO_3S$ (molecular weight: 281,29): calculated: C 64.05, H 2.51, N 4.98, O 17.06, S 11.40%, found C 63.87, H 2.79, N 4.98, O 17.17, S 11.25%.

EXAMPLE 2

(a) 15 g (72.7 mmol) of 3-nitrophthalic acid N-methylimide and 18.1 g (91 mmol) of disodium thiosalicylate are stirred under reflux in 750 ml of tetrahydrofuran (THF) for one day. After cooling, 2N hydrochloric acid and toluene are added to the mixture. The organic extracts are dried and evaporated. After recrystallisation from dioxane, 15.54 g (68% of theory) of 3-(2-carboxyphenylthio)-phthalic acid N-methylimide are obtained; melting point: 270°-272° C.

Analysis for $C_{16}H_{11}NO_4S$ (molecular weight: 313.33). calculated: C 61.34, H 3.54, N 4.47, S 10.23%, found: C 61.00, H 3.60, N 4.80, S 9.90%.

(b) 15.5 g (49.5 mmol) of 3-(2-carboxyphenylthio)-phthalic acid N-methylimide are converted into the acid chloride by boiling with 400 ml of THF and 150 ml of oxalyl chloride. After the mixture has been refluxed for 5 hours, 150 ml of chlorobenzene are added and the mixture is evaporated to a total volume of 150 ml. 13.2 g (98.9 mmol) of anhydrous aluminium chloride are added to the cooled suspension. The mixture is stirred at 25° C. for 18 hours and is then evaporated. The residue is taken up in 2N hydrochloric acid and extracted with THF/toluene. The extracts are washed with saturated NaHCO$_3$ solution, dried over sodium sulfate and evaporated. After recrystallisation from dioxane, 5 g (34% of theory) of thioxanthone-3,4-dicarboxylic acid N-methylimide are obtained; melting point: 287°-288° C.

Analysis for $C_{16}H_9NO_3S$ (molecular weight: 295.31): calculated: C65.08, H 3.07, N 4.74, S 10.86%, found: C 65.03, H 3.16, N 4.75, S 10.65%.

EXAMPLE 3

4.80 g (17.1 mmol) of thioxanthone-3,4-dicarboxylic acid imide are refluxed in 511 ml of 0.1N NaOH solution for 90 minutes. The resulting mixture of amide acid and dicarboxylic acid sodium salts is acidified with concentrated hydrochloric acid and refluxed for 18 hours. The crude thioxanthone-3,4-dicarboxylic acid is filtered off, washed with water and converted into anhydride by refluxing in xylene with 11 ml of acetic anhydride, and the anhydride is precipitated after partial evaporation of the solution. 4.32 g (90% of theory) of thioxanthone-3,4-dicarboxylic acid anhydride are obtained; melting point: 330°–301° C.

Analysis for $C_{15}H_6O_4S$ (molecular weight: 282.27): calculated: C 63.83, H 2.14, O 22.67, S 11.36%, found: C 63.97, H 2.01, O 22.61, S 11.13%.

EXAMPLES 4–14

2 g (7.1 mmol) of thioxanthone-3,4-dicarboxylic acid anhydride, 0.92 g (7.1 mmol) of 2-ethyl-1-hexylamine and 20 ml of xylene are refluxed for 30 minutes, using a water separator. On cooling, 2.35 g (85% of theory) of thioxanthone-3,4-dicarboxylic acid N-(2-ethyl-n-hexyl)-imide precipitate; melting point: 189°–190° C.

Analysis for $C_{23}H_{23}NO_3S$ (molecular weight 393.50): calculated: C 70.20, H 5.89, N 3.56, S 8.15%, found: C 70.05, H 5.57, N 3.54, S 8.17%.

Thioxanthone-3,4-dicarboxylic acid imides shown in Table I which follows are prepared in an analogous manner. Different reaction conditions are likewise shown in the table.

EXAMPLE 16

30.0 g (106 mmol) of thioxanthone-3,4-dicarboxylic acid anhydride and 265.7 ml of 2N NaOH solution are refluxed until a clear solution is obtained. After 45 minutes, the solution is cooled to 25° C. and the product is filtered off, washed with ethanol, dried and recrystallised from ethanol/water. Disodium thioxanthone-3,4-dicarboxylate (hemi-hydrate) is obtained in quantitative yield; melting point: >350° C.

Analysis for $C_{15}H_6Na_2SO_5.\frac{1}{2}H_2O$ (molecular weight: 353.25): calculated: C 51.00, H 1.99, Na 13.00, S 9.07%, found: C 50.87, H 2.11, Na 12.95, S 8.96%.

EXAMPLE 17

4.0 g (14.2 mmol) of thioxanthone-3,4-dicarboxylic acid imide, 4.12 g (21.3 mmol) of 1-octyl bromide, 5.89 g (42.7 mmol) of potassium carbonate and 40 ml of DMF are stirred at 80° C. for 1 day. The mixture is evaporated, the residue is taken up in 2N hydrochloric acid and the mixture is extracted with methylene chloride. The organic phases are washed with saturated $NaHCO_3$ solution and saturated NaCl solution, dried and evaporated. After recrystallisation from cyclohexane, 5.28 g (95% of theory) of thioxanthone-3,4-dicarboxylic acid N-n-octylimide are obtained; melting point: 188°–190° C.

Analysis for $C_{23}H_{23}NO_3S$ (molecular weight: 393.50): calculated: C 70.20, H 5.89, N 3.56, O 12.20, S 8.15%, found: C 70.05, H 5.86, N 3.71, O 12.77, S 8.11%.

TABLE 1

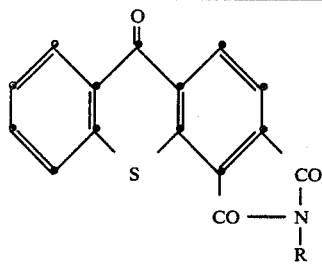

| Example No. | R | Yield % of theory | M.p. °C. | Comments |
|---|---|---|---|---|
| 5 | —C(CH$_3$)$_2$—CH$_2$—C(CH$_3$)$_3$ | 77 | 237–41 | Reaction in o-dichlorobenzene |
| 6 | (4-methylphenyl) | 49 | 296–99 | recrystallised from dioxane |
| 7 | —CH$_2$CH$_2$OH | 82 | 287–89 | " |
| 8 | —CH$_2$CH$_2$N(CH$_3$)$_2$ | 80 | 235–36 | — |
| 9 | —N(CH$_3$)$_2$ | 83 | 307–8 | — |
| 10 | —CH$_2$CH$_2$SO$_3^-$Na$^+$ | 84 | >330 | recrystallised from H$_2$O/THF |
| 11 | —CH$_2$CH$_2$CH$_2$N(CH$_3$)$_2$ | 45 | 186–8 | — |
| 12 | —CH$_2$CH$_2$N(C$_2$H$_5$)$_2$ | 81 | 174–6 | recrystallised from dioxane |
| 13 | —CH—CH=CH$_2$ | 75 | 242–4 | — |
| 14 | —CH$_2$—C≡CH | 57 | >310 | — |
| 15 | —CH(CH$_3$)$_2$ | 81 | 280–290 | Reaction in o-dichlorobenzene, recrystallised from CH$_2$Cl$_2$/pentane |

EXAMPLE 18

(a) 1.47 g (5 mmol) of 3,5-dinitrophthalic acid N-n-butylimide, 1.24 g (6 mmol) of disodium thiosalicylate and 15 ml of THF are stirred under reflux for 5 hours. 15 ml of THF, 10 ml of 2N hydrochloric acid and 30 ml of toluene are then added, the mixture is shaken and the organic phase is separated off, washed with saturated NaCl solution, dried and evaporated. After recrystallisation from THF/toluene, 1.80 g (90% of theory) of 5-nitro-3-(2-carboxyphenylthio)-phthalic acid N-n-butylimide are obtained; melting point: 192°–196° C.

Analysis for $C_{19}H_{16}N_2O_6S$ (molecular weight: 400.41): calculated: C 57.00, H 4.03, N 7.00, S 8.01%, found: C 56.82, H 4.10, N 6.95, S 7.72%.

(b) 20.0 g (50 mmol) of 5-nitro-3-(2-carboxyphenylthio)-phthalic acid N-n-butylimide are stirred with 80 g of polyphosphoric acid at 180° C. for 3 hours. The mixture is cooled and 300 ml of water are carefully added. The precipitate is filtered off, washed with water and dried in vacuo at 150° C. When the product is recrystallised from toluene, 12.3 g (64% of theory) of 1-nitrothioxanthone-3,4-dicarboxylic acid N-n-butylimide are obtained; melting point: 264°–266° C.

Analysis for $C_{19}H_{14}N_2O_5S$ (molecular weight: 382.39): calculated: C 59.67, H 3.69, N 7.33, O 20.92, S 8.38%, found: C 59.76, H 3.86, N 7.36, O 20.84, S 8.18%.

EXAMPLE 19

(a) 5.0 g (12 mmol) of 5-nitro-3-(2-carboxyphenylthio)-phthalic acid N-n-butylimide are hydrogenated with 1 g of Pd/C (5% by weight of Pd) in 100 ml of DMF for 8 hours. The catalyst is filtered off and the mother liquor is evaporated. The residue is taken up in water/THF/toluene and the mixture is brought to pH 6. The organic extracts are dried over sodium sulfate and evaporated. When the residue is recrystallised from methylene chloride, 2.34 g (53% of theory) of the crude amino acid are obtained. For characterisation, 1 g (2.7 mmol) of the crude amino acid is kept at 100° C. with 5 ml of acetic anhydride for 30 minutes, after which the mixture is evaporated in vacuo at 80° C. The residue is taken up in hydrochloric acid/THF/toluene and the organic phases are washed with saturated NaCl solution, dried over sodium sulfate and evaporated. After recrystallisation from methylene chloride/n-pentane, 800 mg (72% of theory) of 5-acetylamino-3-(2-carboxyphenylthio)-phthalic acid N-n-butylimide are obtained; melting point: 231°–233° C.

Analysis for $C_{21}H_{20}N_2O_5S$ (molecular weight: 412.46): calculated: C 61.15, H 4.89, N 6.79, O 19.40, S 7.77%, found: C 61.00, H 5.10, N 6.30, O 19.10, S 7.40.

(b) 500 mg (1.35 mmol) of crude 5-amino-3-(2-carboxyphenylthio)-phthalic acid N-n-butylimide and 5 ml of thionyl chloride are refluxed for 1 hour. 10 ml of chlorobenzene are then added and the mixture is evaporated to a total volume of 10 ml. After the mixture has been cooled, 718 mg (5.39 mmol) of anhydrous aluminium chloride are added and the mixture is stirred at 25° C. for 2 hours. The mixture is evaporated, THF/toluene are added and the mixture is brought to pH 6 with water/saturated $NaHCO_3$ solution. The organic extracts are washed with saturated NaCl solution, dried and evaporated. After recrystallisation from THF, 60 mg (13% of theory) of 1-aminothioxanthone-3,4-dicarboxylic acid N-n-butylimide are obtained; melting point: 272°–274° C.

Analysis for $C_{19}H_{16}N_2O_3S$ (molecular weight: 352.41): calculated: C 64.76, H 4.58, N 7.95, O 13.62, found: C 64.29, H 4.56, N 8.02, O 13.96%.

EXAMPLE 20

(a) 20.0 g (49.9 mmol) of 5-nitro-3-(2-carboxyphenylthio)-phthalic acid N-n-butylimide, 9.08 g (54.9 mmol) of n-decanethiol, 27.6 g (199.6 mmol) of potassium carbonate and 500 ml of DMF are stirred at 25° C. for 2 hours. The mixture is evaporated in vacuo and the residue is taken up in methylene chloride/dilute hydrochloric acid. The organic phases are washed with saturated NaCl solution, dried over sodium sulfate and evaporated. After recrystallisation from cyclohexane, 27.56 g (93% of theory) of 5-n-decylthio-3-(2-carboxyphenylthio)-phthalic acid N-n-butylimide are obtained; melting point: 113°–115° C.

Analysis for $C_{29}H_{35}NO_4S_2$ (molecular weight: 525.72): calculated: C 66.26, H 6.71, N 2.66, S 12.15, O 12.13%, found: C 66.23, H 7.01, N 2.70, S 12.09, O 11.97%.

(b) 11.01 g (21.7 mmol) of 5-n-decylthio-3-(2-carboxyphenylthio)-phthalic acid N-n-butylimide are converted into the corresponding acid chloride by boiling with 55 ml of oxalyl chloride for 1 hour. 120 ml of chlorobenzene are then added and the mixture is evaporated to a total of 120 ml. After the mixture has been cooled, 8.68 g (65.1 mmol) of anhydrous aluminium chloride are added. After stirring at 25° C. for 30 minutes, the mixture is evaporated, the residue is taken up in 2N hydrochloric acid/THF/toluene and the organic phases are washed with $NaHCO_3$ solution and saturated NaCl solution, dried and evaporated. After recrystallisation of the residue from cyclohexane, 10.34 g (95% of theory) of 1-n-decylthiothioxanthone-3,4-dicarboxylic acid N-n-butylimide are obtained; melting point: 143°–145° C.

Analysis for $C_{29}H_{35}NO_3S_2$ (molecular weight: 509.72): calculated: C 68.33, H 6.92, N 2.75 S 12.58%, found: C 68.30, H 6.88, N 2.76, S 12.28%.

EXAMPLE 21

(a) 12.81 g (32 mmol) of 5-nitro-3-(2-carboxyphenylthio)-phthalic acid N-n-butylimide, 3.88 g (35.2 mmol) of thiophenol, 13.27 g (96 mmol) of potassium carbonate and 120 ml of DMF are reacted analogously to Example 19a) and the mixture is worked up. After recrystallisation of the product from toluene/cyclohexane, 13.52 g (91% of theory) of 5-phenylthio-3-(2-carboxyphenylthio)-phthalic acid N-n-butylimide are obtained; melting point: 154°–156° C.

Analysis for $C_{25}H_{21}NO_4S_2$ (molecular weight: 463.57): calculated: C 64.77, H 4.57, N 3.02, S 12.83%, found: C 64.96, H 4.73, N 3.20, S 13.62%.

(b) 12.51 g (27 mmol) of 5-phenylthio-3-(2-carboxyphenylthio)-phthalic acid N-n-butylimide are reacted analogously to Example 19(b). After recrystallisation of the product from toluene, 11.1 g (92% of theory) of 1-phenylthiothioxanthone-3,4-dicarboxylic acid N-n-butylimide are obtained; melting point: 265°–268° C.

Analysis for $C_{25}H_{19}NO_3S_2$ (molecular weight: 445.55): calculated: C 67.39, H 4.30, N 3.14, S 14.39%, found: C 67.28, H 4.29, N 3.16, S 14.13%.

EXAMPLE 22

3.0 g (10.2 mmol) of thioxanthone-3,4-dicarboxylic acid-N-methylimide are initially introduced into a pressure vessel and 30 ml of dimethylamine are condensed into the vessel at −10° C. The mixture is kept under pressure at 25° C. for 10 days. The dimethylamine is evaporated off. After recrystallization of the residue from THF, 2.71 g (78% of theory) of 3-N,N-dimethylcarbamoyl-4-N-methylcarbamoylthioxanthone are obtained; decomposition point, to the educt, from 185° C.

Analysis for $C_{18}H_{16}N_2O_3S$ (molecular weight: 340.40): calculated: C 63.52, H 4.74, N 8.23, O 14.10, S 9.42%, found: C 63.14, H 4.77, N 8.01, O 14.45, S 9.33%.

EXAMPLE 23

1.0 g (3.5 mmol) of thioxanthone-3,4-dicarboxylic acid anhydride is refluxed with 20 ml of absolute ethanol for 3 hours. The mixture is evaporated in vacuo at a maximum temperature of 60° C. Dilute hydrochloric acid and methylene chloride are added to the residue. The organic phases are dried and concentrated. The 100 MHz-$^1$H-NMR spectrum shows a mixture of the two thioxanthone-3,4-dicarboxylic acid monoethyl esters in a ratio of about 2:1 (3-ester:4-ester). The 3-ester is obtained in virtually pure form by recrystallisation from methylene chloride/n-pentane; yield: 790 mg (68% of theory); melting point: 315°–319° C.

Analysis for $C_{17}H_{12}O_5S$ (molecular weight 328.34): calculated: C 62.19, H 3.69, O 24.37, S 9.77% found: C 61.82, H 3.77, O 24.48, S 9.69%.

EXAMPLE 24

2.9 g (10.3 mmol) of thioxanthone-3,4-dicarboxylic acid anhydride, 58 ml of n-butanol, 15 ml of toluene and 0.87 ml of concentrated sulfuric acid are boiled for 20 hours, using a water separator. The mixture is partly evaporated and the residue is taken up in water/methylene chloride. The organic extracts are washed with brine, dried over sodium sulfate and evaporated. The residue is dried under a high vacuum at 150° C., 3.92 g (92% of theory) of di-n-butyl thioxanthone-3,4-dicarboxylate of melting point 49°–51° C. being obtained.

Analysis for $C_{23}H_{24}O_5S$ (molecular weight: 412.50): calculated: C 66.97, H 5.86, O 19.39, S 7.77%, found: C 67.10, H 5.88, O 19.14, S 7.63%.

EXAMPLE 25

1 g (3.5 mmol) of thioxanthone-3,4-dicarboxylic acid anhydride, 5 ml of diethylene glycol monomethyl ether and 5 drops of concentrated sulfuric acid are reacted as described in Example 23, and the product is isolated. 863 mg (48% of theory) of bis-[2-(2-methoxyethoxy)ethyl] thioxanthone-3,4-dicarboxylate (liquid, partly crystallises after some weeks) are obtained.

Analysis for $C_{25}H_{28}O_9S$ (molecular weight: 504.55): calculated: C 59.51, H 5.59%, found: C 59.30, H 5.50%.

EXAMPLE 26

2.30 g (10 mmol) of 4,5-dichlorophthalic acid N-methylimide, 2.69 g (13 mmol) of disodium thiosalicylate and 12 ml of DMF are stirred at 80° C. for 18 hours. The mixture is taken up in dilute hydrochloric acid/THF/toluene. The organic phases are separated off and extracted with NaHCO$_3$ solution. The basic aqueous extracts are acidified and extracted with THF/toluene. The extracts are dried and evaporated. The residue is subjected to fractional crystallisation from THF/toluene. 1.1 g (32% of theory) of crude 4-(2-carboxyphenylthio)-5-chlorophthalic acid N-methylimide are thus obtaind. This is heated at 200° C. in 12 g of polyphosphoric acid for 10 minutes. The mixture is cooled, taken up in water and extracted with THF/toluene. The extracts are washed with NaHCO$_3$ solution and saturated NaCl solution, dried over sodium sulfate and evaporated. After recrystallisation from THF/toluene, 580 mg (55% of theory) of 4-chlorothioxanthone-1,2-dicarboxylic acid N-methylimide are obtained; melting point: 258°–266° C.

Analysis for $C_{16}H_8ClNO_3S$ (molecular weight: 329.76): calculated: C 58.28, H 2.45, N 4.25%, found: C 58.53, H 2.74, N 4.32%.

EXAMPLE 27

1.65 g (8 mmol) of 3-nitrophthalic acid N-methylimide, 1.60 g (8.7 mmol) of disodium salicylate and 10 ml of N,N-dimethylacetamide are stirred at 120° C. for 30 minutes. After cooling, the mixture is taken up in dilute hydrochloric acid/THF/toluene, the organic extracts are extracted with NaHCO$_3$ solution and the aqueous basic extracts are acidified and extracted with THF/toluene. The extracts are dried over sodium sulfate and evaporated, excess salicylic acid being sublimed off. The residue (1.57 g, maximum of 5.2 mmol) is heated at 150° C. in 14 g of polyphosphoric acid for 90 minutes. The mixture is cooled, taken up in water/THF/toluene, brought to pH 10 and extracted. The organic phases are washed with NaHCO$_3$ solution and saturated NaCl solution, dried over sodium sulfate and evaporated. When the residue is recrystallised from THF, 340 mg (23% of theory) of xanthone-3,4-dicarboxylic acid N-methylimide are obtained; melting point: 280°–283° C.

Analysis for $C_{16}H_9NO_4$ (molecular weight: 279.25): calculated: C 68.82; H 3.25, N 5.02%, found: C 68.62, H 3.04, N 5.22%.

EXAMPLE 28

3.0 g (7.8 mmol) of 1-nitrothioxanthone-3,4-dicarboxylic acid N-n-butylimide and 2.2 g (15.9 mmol) of potassium carbonate are stirred in 35 ml of DMF at 50° C. for 1 hour. The mixture is evaporated, the residue is taken up in dilute HCl solution and the mixture is extracted with THF and toluene. After drying over sodium sulfate, the extracts are evaporated. Recrystallisation of the residue from THF gives 2.04 g (74% of theory) of 1-hydroxythioxanthone-3,4-dicarboxylic acid N-n-butylimide; melting point: 191°–193° C.

Analysis for $C_{19}H_{15}NO_4S$ (molecular weight: 353.39): calculated: C 64.58 H 4.28 N 3.97 S 9.07% found: C 64.29 H 4.39 N 3.85 S 8.83%.

EXAMPLE 29

13.01 g (40 mmol) of thioxanthone-3,4-dicarboxylic acid N-(2-hydroxyethyl)-imide are added to a solution of 15.75 g (150.7 mmol) of freshly distilled methacrylyl chloride in 130 ml of absolute dioxane. 2 ml of pyridine are added to the mixture, and the mixture is refluxed for 4 hours. It is then evaporated at 50°0 C. in vacuo, the residue is taken up in methylene chloride/water an the organic phases are dried and evaporated. When the residue is recrystallised from methylene chloride/n-pentane, 11.84 g (71% of theory) of thioxanthone-3,4-dicarboxylic acid N-(2-methacryloxyethyl)-imide are obtained; melting point: 201°–206° C.

Analysis for $C_{21}H_{15}NO_5S$ (molecular weight: 393.41): calculated: C 64.12, H 3.85, N 3.56, S 8.15 found: C 63.39, H 3.65, N 3.84, S 8.04%.

EXAMPLES 30 AND 31

1 g (3.7 mmol) of 4-chlorophthalic acid N-benzylimide, 1.46 g of disodium thiosalicylate and 10 ml of DMF are refluxed for 4 hours. After evaporation, the residue is taken up in $NaHCO_3$ solution, this mixture is extracted with THF/toluene, the extracts are discarded and the aqueous phase is then acidified, and the intermediate is extracted with THF/toluene. Evaporation gives crude 4-(2-carboxyphenylthio)-phthalic acid N-benzylimide. This is stirred with 14.8 g of polyphosphoric acid at 200° C. for 30 minutes. The mixture is cooled, stirred with water and brought up pH 8 and the precipitate is filtered off and dried. The crude product is chromatographed over silica gel using methylene chloride. The two products formed are thereby separated:

Thioxanthone-2,3-dicarboxylic acid N-benzylimide, 120 mg (9% of theory), melting point: 289°–294° C.

Analysis for $C_{22}H_{13}NO_3S$ (molecular weight: 371.41): calculated: C 71.15, H 3.53, N 3.77%, found: C 71.62, H 3.91, N 3.60%.

Thioxanthone-1,2-dicarboxylic acid N-benzylimide; 40 mg (3% of theory); melting point: 210°–213° C,; found C 70.78 H 4.17 N 3.66%

(Allocation by means of the $^1$NMR spectrum).

The 4-chlorophthalic acid N-benzylimide is prepared by refluxing 4-chlorophthalic anhydride (13 g; 71.2 mmol) with 7.63 g (71.2 mmol) of benzylamine in xylene, the water being separated off. After evaporation of the mixture and recrystallisation of the residue from toluene/cyclohexane, 18.01 g (93% of theory) of 4-chlorophthalic acid N-benzylimide are obtained; melting point: 117°–119° C.

Analysis for $C_{15}H_{10}ClNO_2$ (molecular weight: 271.70): calculated: C 66.31, H 3.71, N 5.16, Cl 13.05%, found: C 65.90, H 3.80, N 5.40, Cl 13.00%.

EXAMPLES 32 AND 33

5 g (17.71 mmol) of thioxanthone-3,4-dicarboxylic acid anhydride and 50 ml of absolute ethanol are refluxed for 5 hours. The mixture is evaporated to dryness in vacuo and the residue (mixture of the two half-esters) is refluxed with 65 ml of thionyl chloride for 30 minutes. The mixture is evaporated again and the residue is refluxed with 60 ml of absolute ethanol for 4 hours. The mixture is concentrated, the residue is dissolved in THF/toluene 1:1, the solution is washed twice with $NaHCO_3$ solution and the organic phases are dried over sodium sulfate and evaporated. When the residue is recrystallised from $CH_2Cl_2$/pentane, 3.4 g (54%) of diethyl thioxanthone-3,4-dicarboxylic acid are obtained, melting point: 100°–101° C.

Dimethyl thioxanthone-3,4-dicarboxylic acid is prepared analogously to the diethyl ester, yield: 52%, melting point: 150°–55° C.

EXAMPLE 34

5 g (15.24 mmol) of dimethyl thioxanthone-3,4-dicarboxylic acid are dissolved in 50 ml of absolute allyl alcohol. 0.4 g (7.4 mmol) of $NaOCH_3$ are added under reflux and the mixture is refluxed for 1 day. The suspension is taken up in THF/toluene 1:1 and the mixture is washed three times with $NaHCO_3$ solution. After drying over sodium sulfate, the solution is evaporated and the residue is recrystallised from methylene chloride/pentane. Yield of diallyl thioxanthone-3,4-dicarboxylic acid 3.0 g (52%), melting point: 45°–8° C.

EXAMPLE 35

10.0 g (40 mmol) of 5-carboxy-3-nitrophthalic acid N-methylimide (prepared according to: M. A. Ribi, C. C. Wei and E. H. White, Tetr. 28, 481 (1972)), 100 ml of dimethylsulfoxide, 4.85 g (44 mmol) of thiophenol and 17.69 g (128 mmol) of anhydrous potassium carbonate are stirred at 25° for 5 hours. The mixture is discharged onto 300 ml of $H_2O$ and acidified. The precipitate filtered off, washed with $H_2O$ and taken up in methylene chloride. After drying over sodium sulfate, the mixture is evaporated and the residue is recrystallised from methylene chloride/pentane, yield: 8.0 g (64%) of 5-carboxy-3-phenylthiophthalic acid N-methylimide, melting point: 287°–92° C.

0.50 g (1.6 mmol) of the above imide is refluxed with 3.25 ml (6.5 mmol) of 2N NaOH solution for 80 minutes. The mixture is highly acidified with concentrated HCl solution and refluxed for 18 hours. The mixture is poured onto water and extracted with THF/toluene. The extracts are dried over $Na_2SO_4$ and evaporated. The residue (crude tricarboxylic acid) is heated with 8 ml of o-dichlorobenzene and 0.5 ml of acetic anhydride, with azeotropic removal of the water and glacial acetic acid, for 5 hours. After evaporation of the mixture and addition of a little pentane, 0.31 g (65%) of 5-carboxy-3-phenylthiophthalic anhydride is obtained, melting point: 237°–47° C.

0.13 g (0.43 mmol) of the above anhydride is heated at 220° C. in 1.3 g of polyphosphoric acid for 2 hours. The mixture is cooled, diluted with water and extracted with THF/toluene. The extracts are dried over $Na_2SO_4$ and evaporated. When the residue is recrystallised from THF/toluene/pentane, 0.10 g (77%) of thioxanthone-1,3-dicarboxylic acid is obtained, melting point: 325°–30° C.

Analysis for $C_{15}H_8O_5S$ (molecular weight: 300.28) calculated: C 60.00, H 2.69, O 26,64, S 10.68%, found: C 59.00, H 3.23, O 25.52, S 10.00%.

USE EXAMPLE I (a) Preparation of the polymer

A polymer having the following structure and composition is prepared:

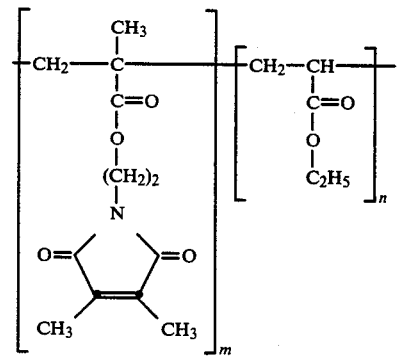

$$\frac{m}{m+n} = 0.8$$

$$\frac{N}{m+n} = 0.2$$

465.5 g (1.963 mol) of dimethylmaleinimidyl-$\beta$-(methacryloyloxy)-ethyl ester (prepared according to German Offenlegungsschrift 2,626,769) are dissolved in 960 ml of 1-acetoxy-2-ethoxyethane together with 49.15 g (0.49 mol) of ethyl acrylate, under nitrogen. A solution of 3.86 g of azosiobutyronitrile in 25 ml of 1-acetoxy-2-ethoxyethane is allowed to run in 80° C., under a nitrogen atmosphere, and the mixture is then polymerised for 6 hours. The still hot solution is stabilised with 2.57 g of 2,6-di-tert.-butyl-p-cresol. The average molecular weight of the polymer thus obtained (determined by light scattering measurement in $CHCl_3$) and its limiting viscosity $\eta_{limit}$ are:

| average molecular weight (light scattering measurement in $CHCl_3$) | $\eta_{limit}$ dl/g | ($CHCl_3$) |
|---|---|---|
| $1.8 \times 10^5$ | 0.17 | 20° C. |

(b) Production of images

The amounts of sensitiser shown in Table II which follows are added to 10 g of the polymer solution described above in 1-acetoxy-2-ethoxyethane, diluted with N,N-dimethylformamide, the amount (concentration) being based on the solids content. The polymer solutions with the dissolved sensitiser are applied to copper-coated epoxide sheets by centrifugation (500 revolutions/minute for 1 minute) such that, after drying (15 minutes at 80° C.), a 1–3$\mu$ thick polymer layer is formed on the copper. The coated sheets are exposed to a 400 watt high-pressure mercury lamp at a distance of 55 cm from the vacuum bench through a negative slide (step wedge: Stouffer 21-step sensitivity guide). A Pyrex glass filter 8 mm thick is inserted in front of the vacuum bench; for the exposure times, see Table II.

After the exposure, the image is developed in a 1,1,1-trichloroethane bath for 2 minutes, the non-crosslinked portions being dissolved out. The resulting relief image of the step wedge defined is rendered visible by etching the blank copper parts with 50% $FeCl_3$ solution. In Table II which follows, $S_{rel}$ is the relative sensitivity. It is a factor indicating by how much longer or shorter than 3 minutes exposure must be carried out for stage 7 (optical density of the step wedge = 1) still to be defined. The following relationship applies:

$$S_{rel} = \frac{1}{\sqrt{2}^{(7-X)}},$$

in which X is the actual step defined after exposure for 1 minute. The determination of $S_{rel}$ is based on the method for determining photosensitivity described by W. S. De Forest ("Photoresist", McGraw Hill Book Company, New York, 1975, pages 113 et seq.).

TABLE II

| Sensitiser according to Example No. | $\lambda_{max}$ | $\epsilon_{max}$ | Sensitiser concentration | | Last step defined after 1 minute | $S_{abs.}$ % | $S_{rel.}$ |
|---|---|---|---|---|---|---|---|
| | | | % by weight | mol % | | | |
| 1 | 420 | 5200 | 1.41 | 0,005 | 13 | 567 | 8 |
| 2 | 420 | 4800 | 1.48 | 0,005 | 12 | 401 | 5.66 |
| 3 | 423 | 4900 | 1.41 | 0,005 | 8 | 100 | 1.41 |
| 4 | 420 | 4600 | 1.97 | 0,005 | 9 | 200 | 2.00 |
| 5 | 419 | 5000 | 1.97 | 0,005 | 12 | 566 | 5.66 |
| 7 | 420 | 4800 | 1.63 | 0,005 | 12 | 566 | 5.60 |
| 13 | 420 | 4800 | 1.61 | 0,005 | 13 | 800 | 8.00 |
| 14 | 421 | 5200 | 1.6 | 0,005 | 11 | 400 | 4.00 |
| 16 | 418 | 4800 | 1.97 | 0,005 | 12 | 401 | 5.66 |
| 21 | 388 | 6000 | 1.70 | 0,005 | 10 | 201 | 2.83 |

TABLE II-continued

| Sensitiser according to Example No. | $\lambda_{max}$ | $\epsilon_{max}$ | Sensitiser concentration | | Last step defined after 1 minute | $S_{abs.}$ % | $S_{rel.}$ |
|---|---|---|---|---|---|---|---|
| | | | % by weight | mol % | | | |
| 23 | 397 | 6080 | 2.06 | 0,005 | 12 | 566 | 5.66 |
| 24 | 398 | 4300 | 2.52 | 0,005 | 12 | 566 | 5.66 |
| 25 | 399 | 3400 | 1.65 | 0,005 | 12 | 566 | 5.66 |

USE EXAMPLE II

Production of Metallic Images (a) Preparation of the matrix polymer 125.9 g of hydroxypropyl methacrylate (mixture of the 2- and 3-hydroxypropyl esters) and 58.3 g of methyl methacrylate are dissolved in 416 ml of dioxane, the solution is heated to 70° C., while stirring and under an inert gas, and 0.92 g of azoisobutyronitrile is then added. After 12 hours at 70° C., the mixture is diluted with 500 ml of dioxane. The polymer is then isolated by precipitation in 6 liters of ice-water. Yield: 169.3 g (91.5% of theory). Glass transition point: 90° C.; $[\eta]=0.65$ dl/g in N,N-dimethylformamide at 25° C.; average molecular weight: 120,000 (determined by light scattering).

(b) Production of metallic images

The polymer prepared according to (a) is dissolved in N,N-dimethylformamide, and in each case 5% by weight of the thioxanthone compound shown in Table III which follows and the equimolar amount of copper-II acetate are added. The solids content of the solution is 30% by weight. A polyester foil is then coated with a 50 $\mu$m thick wet film of the solution, using a roller coater, and exposed to light at 90° C. through a mask (21-step sensitivity guide from Stouffer) on a vacuum heating stage. A 5 kW high-pressure mercury lamp (Staub AG, Neu-Isenburg, Federal Republic of Germany) is used as the light source. The image of copper nuclei thus obtained is thickened to a metallic, electrically conductive image at 49° C. in an electroless metal deposition bath having the following composition: 12 g of copper sulfate/liter, 8 g of formaldehyde/liter, 15 g of NaOH/liter, 14 g of sodium potassium tartrate/liter, 20 g of ethylenediaminetetraacetic acid/liter and 1 g of octylphenol polyethylene glycol ether/liter (n ~ 1; Tryton X 100® from Röhm & Haas). The results are shown in Table III.

TABLE III

| Compound according to Example No. | Exposure time seconds | Last step defined |
|---|---|---|
| 4 | 360 | 8 |
| 16 | 360 | 4 |
| 23 | 360 | 7 |
| 24 | 360 | 2 |

USE EXAMPLE III

Photocurable Composition

A white varnish is prepared according to the following recipe:

17.6 g of Ebecryl 593 (polyester acrylate resin from UCB, Belgium),
11.8 g of N-vinylpyrrolidine,
19.6 g of titanium dioxide RTC-2 (titanium dioxide from Thioxide, England), 19.6 g of Sachtolith HDA (lithopones from Sachtleben Chemie, Duisburg, Federal Republic of Germany),
11.8 g of trimethylolpropanetrisacrylate,
19.6 g of Setalux UV 2276 (acrylated epoxide resin based on bisphenol A; Kunstharzfabrik Synthese, Bergen, Holland).

The above components are ground, together with 125 g of glass beads (diameter 4 cm), in a 250 ml glass bottle for at least 24 hours. 2% by weight of the photo-curing agent described below and in each case 0.25% by weight of the sensitisers shown below (co-initiators) are dissolved in one part by weight of the white varnish stock paste thus obtained. The mixture is then ground again with glass beads for 16 hours.

The white varnishes thus prepared are applied to sheets of glass with a 30 μm doctor blade. The samples are exposed to 80 W/cm with a lamp using a PPG irradiation instrument, and the rate of curing which can be achieved whilst maintaining the resistance to wiping is determined.

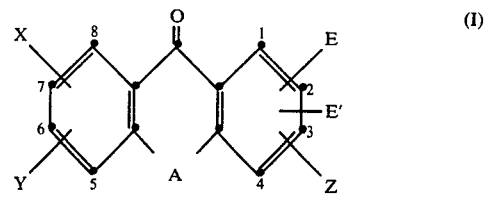

in which A is —O— or —S—, X and Y independently of one another are hydrogen, $C_{1-20}$-alkyl, halogen, —OR', —SR' or —NO$_2$, Z is hydrogen, $C_{1-4}$-alkyl, halogen, —OR', —SR', —NO$_2$, —NH$_2$, —OH or —NHCOCH$_3$, E and E' together are —CO—O—CO— or —CO—N(R)—CO—, R is hydrogen, $C_{1-20}$-alkyl, phenyl, alkylphenyl having 1-4 C atoms in the alkyl moiety, phenethyl, benzyl, cyclohexyl, —(CH$_2$)$_n$—Q, $C_{2-6}$-alkenyl, propargyl, —N(CH$_3$)$_2$, —OH or $C_{1-10}$-alkoxy, R' is $C_{1-20}$-alkyl, phenyl, halogenophenyl, nitro-

| Photo-curing agent 2% by weight | Sensitiser 0.25% by weight | Rate of curing |
|---|---|---|
| CH$_3$—S—⟨phenyl⟩—C(O)—C(CH$_3$)$_2$—N(morpholine) | ⟨thioxanthone⟩ with CO—N(CH$_2$CH=CH$_2$)—CO | 90 m/minute |
| CH$_3$—S—⟨phenyl⟩—C(O)—C(CH$_3$)$_2$—N(morpholine) | ⟨thioxanthone⟩ with COO(CH$_2$)$_2$O(CH$_2$)$_2$OCH$_3$ (two groups) | 60 m/minute |

The 2-methyl-1-[4-methylthio(phenyl)]-2-morpholinopropan-1-one used as the photo-curing agent can be prepared as follows:

151.4 g (0.675 mol) of 3,3-dimethyl-2-methoxy-2-[4-(methylthio)phenyl]-oxirane (melting point: 62°–64° C.) are dissolved in 235.2 g (2.70 mol) of morpholine and the solution is refluxed.

After 15 hours, the mixture is cooled and the morpholine is distilled off. The residue (melting point: 67°–71° C.) is taken up in diethyl ether and extracted with dilute hydrochloric acid. The hydrochloric acid solution is rendered alkaline and extracted with diethyl ether. The ether solution is dried with Na$_2$SO$_4$ and concentrated. The residue can be recrystallised from ethanol. Melting point: 75°–76° C.

What is claimed is:

1. A compound of the formula I phenyl, alkyl- or alkoxy-phenyl having in each case 1–4 C atoms in the alkyl or alkoxy moiety, benzyl or phenethyl, n is the number 1, 2 or 3, Q is —OH, —N($C_{1-2}$-alkyl)$_2$, —SO$_3$—M+, —OCOCH=CH$_2$ or —O-COC(CH$_3$)=CH$_2$ and M+ is an alkali metal cation.

2. A compound of the formula I according to claim 1, in which X and Y are hydrogen, A is —S— and halogen atoms Z or halogen substituents in Z are fluorine, chlorine or bromine.

3. A compound of the formula I according to claim 1, in which X and Y are hydrogen, A is —S—, Z is hydrogen, chlorine, —NO$_2$, —NH$_2$, —OH, —OR' or —SR', R' is $C_{1-10}$-alkyl, benzyl, phenyl or tolyl.

4. A compound according to claim 1, of the formula Ia

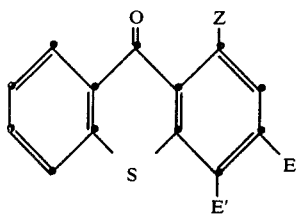

(Ia)

in which Z is hydrogen, chlorine, $-NO_2$, $-NH_2$, $-OH$ or $-SR'$, $R'$ is $C_{1-10}$-alkyl or phenyl and R is as defined in claim 1.

5. A compound of the formula Ia according to claim 4, in which Z is hydrogen and R is hydrogen, $C_{1-10}$-alkyl, phenyl, tolyl, benzyl, $-(CH_2)_n-OH$, $-(CH_2)_n N(C_{1-2}\text{-alkyl})_2$ wherein $n=2$ or 3, $-CH_2CH_2OCOC(CH_3)=CH_2$, allyl or propargyl.

6. A compound of the formula Ia according to claim 4, in which Z is hydrogen and E and E' together are $-CO-N(CH_2CH=CH_2)-CO-$.

7. The compound of claim 2 wherein said halogen atoms Z or halogen substituents in Z are chlorine or bromine.

* * * * *